United States Patent
Liu et al.

(10) Patent No.: US 8,149,273 B2
(45) Date of Patent: Apr. 3, 2012

(54) SYSTEM AND METHODS FOR VITAL SIGN ESTIMATION FROM PASSIVE THERMAL VIDEO

(75) Inventors: Qiong Liu, Milpitas, CA (US); Ming Yang, Evanston, IL (US); Althea Turner, Menlo Park, CA (US)

(73) Assignee: Fuji Xerox Co., Ltd., Tokyo (JP)

( * ) Notice: Subject to any disclaimer, the term of this patent is extended or adjusted under 35 U.S.C. 154(b) by 905 days.

(21) Appl. No.: 12/171,273

(22) Filed: Jul. 10, 2008

(65) Prior Publication Data

US 2009/0141124 A1 Jun. 4, 2009

Related U.S. Application Data

(60) Provisional application No. 60/991,636, filed on Nov. 30, 2007.

(51) Int. Cl.
*A62B 1/04* (2006.01)
*H04N 5/33* (2006.01)
*G06K 9/00* (2006.01)
*A61B 5/04* (2006.01)

(52) U.S. Cl. ........... 348/65; 348/164; 382/128; 600/509

(58) Field of Classification Search .................. None
See application file for complete search history.

(56) References Cited

U.S. PATENT DOCUMENTS

| | | | |
|---|---|---|---|
| 2003/0065269 A1* | 4/2003 | Vetter et al. | 600/503 |
| 2006/0155199 A1* | 7/2006 | Logier et al. | 600/509 |
| 2010/0238294 A1* | 9/2010 | Hogasten et al. | 348/164 |

OTHER PUBLICATIONS

Garbey et al., "Contact-Free Measurement of Cardiac Pulse Based on the Analysis of Thermal Imagery", Aug. 2007, IEEE Transactions on Biomedical Engineering, vol. 54, No. 8.*

N. Sun, M. Garbey, A. Merla, and I. Pavlidis. Estimation of blood flow speed and vessel location from thermal video. Proceedings of the 2004 IEEE Computer Society Conference on Computer Vision and Pattern Recognition, vol. 1, pp. 356-363.

(Continued)

*Primary Examiner* — Wen-Tai Lin
(74) *Attorney, Agent, or Firm* — Sughrue Mion, PLLC

(57) ABSTRACT

A system for measuring a pulse and respiratory rate from passive thermal video includes contour segmentation and tracking, clustering of informative pixels of interests, and robust dominant frequency component estimation. Contour segmentation is used to locate a blood vessel region to measure, after which all pixels in the nearby region are aligned across frames based on the segmentation's position, and scale in each frame. Spatial filtering is then performed to remove noise not related to heart beat and then non-linear filtering is performed on the temporal signal corresponding to each aligned pixel. The signal spectrum of each pixel is then feed to a clustering algorithm for outlier removal. Pixels in the largest cluster are then used to vote for the dominant frequency, and the median of the dominant frequency is output as the pulse rate.

20 Claims, 8 Drawing Sheets

OTHER PUBLICATIONS

N. Sun, M. Garbey, A. Merla, and I. Pavlidis. Imaging the cardiovascular pulse. Proceedings of 2005 IEEE Computer Society Conference on Computer Vision and Pattern Recognition, vol. 2, pp. 416-421.

Marc Garbey, Nanfei Sun, Arcangelo Merla, and Ioannis Pavlidis, Contact-Free measurement of cardiac Pulse Based on the Analysis of thermal Imagery, IEEE Transactions on Biomedical Engineering, Aug. 2007, vol. 54, issue 8, pp. 1418-1426.

S.Y. Chekmenev, A.A. Farag, E.A. Essock. Multiresolution approach for non-contact measurements of arterial pulse using thermal imaging. *CVPR 2006 Workshop*.

S.Y. Chekmenev, A.A. Farag, E.A. Essock. Thermal Imaging of the Superficial Temporal Artery: An Arterial Pulse Recovery Model. *OTCBVS 2007*.

Michael Wübbenhorst, Thermal Wave Techniques, http://www.polymers.tudelft.nl/wubweb/thermalwaves.html.

Oregon State University, Thermal Properties, http://food.oregonstate.edu/energy/t11.html.

D. W. James, The thermal diffusivity of ice and water between −40 and +60° C, Journal of Materials Science, Springer Netherlands, vol. 3, No. 5 / Sep. 1968, pp. 540-543.

\* cited by examiner

SYSTEM AND METHODS FOR VITAL SIGN ESTIMATION FROM PASSIVE THERMAL VIDEO

CROSS REFERENCE TO RELATED APPLICATION

This application claims the benefit of U.S. Provisional Application No. 60/991,636, filed Nov. 30, 2007, the contents of which are herein incorporated by reference in their entirety.

BACKGROUND OF THE INVENTION

1. Field of the Invention

The present invention relates to systems and methods for estimating vital signs from passive thermal video, and more specifically to measuring pulse and respiratory rate from passive thermal video using subject alignment, signal enhancement and harmonic analysis.

2. Background of the Invention

Vital signs are important physiological parameters for health monitoring and emotion recognition. However, wired detection of these parameters limits their feasibility in numerous applications. If these parameters can be detected wirelessly and safely, they can be used more flexibly in many applications, such as airport health screening, elder care, and workplace preventative care.

Sensors for the measurement of the human heart beat and breath rate include the Piezo Pulse Transducer, Piezo Respiratory Transducer, and ECG electrodes. All these measurement sensors have to be attached to a human body and wired to preamps and processing instruments. These measurement approaches place severe restrictions on applications using heart beat and breath rate parameters.

Recently, non-contact measurement methods have been developed. Sun and Garbey et al. did experiments on heart beat measurement with passive thermal video. N. Sun, M. Garbey, A. Merla, and I. Pavlidis; Estimation of blood flow speed and vessel location from thermal video; Proceedings of the 2004 IEEE Computer Society Conference on Computer Vision and Pattern Recognition; vol. 1, pp 356-363; and N. Sun, M. Garbey, A. Merla, and I. Pavlidis; Imaging the cardiovascular pulse; Proceedings of 2005 IEEE Computer Society Conference on Computer Vision and Pattern Recognition; vol. 2, pp 416-421; and Marc Garbey, Nanfei Sun, Arcangelo Merla, and Ioannis Pavlidis; Contact-Free measurement of cardiac Pulse Based on the Analysis of thermal Imagery, IEEE Transactions on Biomedical Engineering; August 2007, vol. 54, issue 8, pp. 1418-1426. These systems are limited for two primary reasons. First, they need artificial markers. Since the artificial markers cannot be at the same location of the detection region (otherwise, the marker will cover the detection region and totally block the signal) and human body is not rigid, the pixel alignment in detection regions based on markers' motion cannot be very accurate for pixel alignment. Inaccurate pixel alignment will cause significant problems for later heartbeat signal detection. Second, Sun et. al's approach of finding the central line of a blood vessel is very sensitive to noise. Wrong detection of the blood vessel central line will lead to pixel misalignment and may ruin the signal detection.

Chekmenev et al. described a Superficial Temporal Artery (STA) measurement model based on arterial wall volumetric change corresponding to blood pressure modulation. S. Y. Chekmenev, A. A. Farag, E. A. Essock; Multiresolution approach for non-contact measurements of arterial pulse using thermal imaging; CVPR 2006 Workshop, and S. Y. Chekmenev, A. A. Farag, E. A. Essock. Thermal Imaging of the Superficial Temporal Artery: An Arterial Pulse Recovery Model. OTCBVS 2007.

In other systems, it is assumed that the measured subject is perfectly static. N. Sun et. al, vol. 1, pp 356-363. That is not true, however, for many pulse rate measurement tasks. Some systems use the hottest pixels to track the center of a blood vessel. N. Sun et. al, vol. 2, pp 416-421; and Marc Garbey et. al, pp. 1418-1426. Since the derivatives around the maximum values are relatively small, tracking based on those hottest spots tends to be noisy. Another system tracks subjects based on foil markers placed on the subject that are not available under most measurement scenarios. See Michael Wübbenhorst; Thermal Wave Techniques; http://www.polymers.tudelft.nl/wubweb/thermalwaves.html.

These earlier approaches involve strong assumptions on subject motion, type and location of blood vessels, etc. Their algorithms also have many parameters that are difficult to incorporate into an automatic detection system. Moreover, the signal detection and denoising model used in these systems are very preliminary, as discussed above. Thus, the existing technology fails to provide an automatic detection system and method that accurately estimates vital sign information using passive thermal video.

SUMMARY OF THE INVENTION

The present invention relates to systems and methods for vital sign estimation by measuring the pulse and respiratory rate from passive thermal video using contour segmentation and tracking, clustering of informative pixels of interests, and robust dominant frequency component estimation. Contour segmentation is used to locate a blood vessel region to measure, after which all pixels in the nearby region are aligned across frames based on the segmentation's position, and scale in each frame. Spatial filtering is then performed to remove noise not related to heart beat and then a spectrum analysis is performed on the temporal signal corresponding to each pixel. The signal spectrum of each pixel is then feed to a clustering algorithm for outlier removal. Pixels in the largest cluster are then used to vote for the dominant frequency, and the median of the dominant frequency is output as the pulse rate In one aspect of the invention, a system for estimating vital signs from passive thermal video comprises an infrared video receiving module for receiving an infrared video segment of a subject; a contour segmentation module for contour segmenting the video segment to select a region of pixels representing a portion of the subject; an alignment module for aligning the selected region of pixels across a plurality of frames of the video segment; a signal detection module for detecting a signal from the selected region using a thermal wave propagation-based signal detection method; a spatial filtering module for spatial filtering the signal to remove noise not related to the vital sign to be measured; a non-linear temporal filtering module to process the temporal signal corresponding to each aligned pixel sequence; a clustering module for removing outliers of the signal using a pixel clustering algorithm; a frequency selection module for selecting a frequency peak of the signal using a dominant frequency voting technique; and an averaging module for averaging the selected frequency peak to compute an average estimation of at least one vital sign.

In another aspect, the contour segmentation module further includes a natural feature module for selecting natural features close to the selected region.

In still another aspect, the contour segmentation module further includes a temperature selection module for selecting an isotherm temperature based on temperature modulation dynamic range and camera sensitivity.

In yet another aspect, the contour segmentation module further includes a contour selection module for selecting a contour line corresponding to the steepest temperature change in the selected region.

In another aspect, the selected region of pixels corresponds to a blood vessel.

In another aspect, the spatial filtering module further includes a frequency response computation module for computing the frequency responses of the signal using a normalized rectangular window and a Hamming window.

In a further aspect of the invention, a method for estimating vital signs from a passive thermal video comprises the steps of receiving an infrared video segment of a subject; contour segmenting the video segment to select a region of pixels representing a portion of the subject; aligning the selected region of pixels across a plurality of frames of the video segment; detecting a signal from the selected region using a thermal wave propagation-based signal detection method; spatial filtering the signal to remove noise not related to the vital sign to be measured; performing non-linear filtering on the signal corresponding to each aligned pixel of the selected region; removing outliers of the signal using a pixel clustering algorithm; selecting a frequency peak of the signal using a dominant frequency voting technique; and averaging the selected frequency peak to compute an average estimation of at least one vital sign.

In a further aspect, the step of contour segmenting the video segment further includes selecting natural features close to the selected region.

In a further aspect, the step of contour segmenting the video segment further includes selecting an isotherm temperature based on temperature modulation dynamic range and camera sensitivity.

In a further aspect, the step of contour segmenting the video segment further includes selecting a contour line corresponding to the steepest temperature change in the selected region.

In a further aspect, the step of contour segmenting the video segment further includes selecting a region of pixels corresponding to a blood vessel.

In a further aspect, the step of spatial filtering the signal to remove noise further includes computing the frequency responses of the signal using a normalized rectangular window and a Hamming window.

In yet another aspect of the present invention, a computer program product embodied on a computer readable medium for estimating vital signs from passive thermal video comprises computer program code for receiving an infrared video segment of a subject; contour segmenting the video segment to select a region of pixels representing a portion of the subject; aligning the selected region of pixels across a plurality of frames of the video segment; detecting a signal from the selected region using a thermal wave propagation-based signal detection method; spatial filtering the signal to remove noise not related to the vital sign to be measured; performing non-linear filtering on the signal corresponding to each aligned pixel of the selected region; removing outliers of the signal using a pixel clustering algorithm; selecting a frequency peak of the signal using a dominant frequency voting technique; and averaging the selected frequency peak to compute an average estimation of at least one vital sign.

In a further aspect, the computer program product further comprises computer program code for contour segmenting the video segment by selecting natural features close to the selected region.

In a further aspect, the computer program product further comprises computer program code for contour segmenting the video segment by selecting an isotherm temperature based on temperature modulation dynamic range and camera sensitivity.

In a further aspect, the computer program product further comprises computer program code for contour segmenting the video segment by selecting a contour line corresponding to the steepest temperature change in the selected region.

In a further aspect, the computer program product further comprises computer program code for selecting a region of pixels that corresponds to a blood vessel.

In a further aspect, the computer program product further comprises computer program code for spatial filtering the signal to remove noise by computing the frequency responses of the signal using a normalized rectangular window and a Hamming window.

Additional aspects related to the invention will be set forth in part in the description which follows, and in part will be obvious from the description, or may be learned by practice of the invention. Aspects of the invention may be realized and attained by means of the elements and combinations of various elements and aspects particularly pointed out in the following detailed description and the appended claims.

It is to be understood that both the foregoing and the following descriptions are exemplary and explanatory only and are not intended to limit the claimed invention or application thereof in any manner whatsoever.

BRIEF DESCRIPTION OF THE DRAWINGS

The accompanying drawings, which are incorporated in and constitute a part of this specification exemplify the embodiments of the invention and, together with the description, serve to explain and illustrate principles of the inventive technique. Specifically.

DETAILED DESCRIPTION OF THE INVENTION

Figure 1:
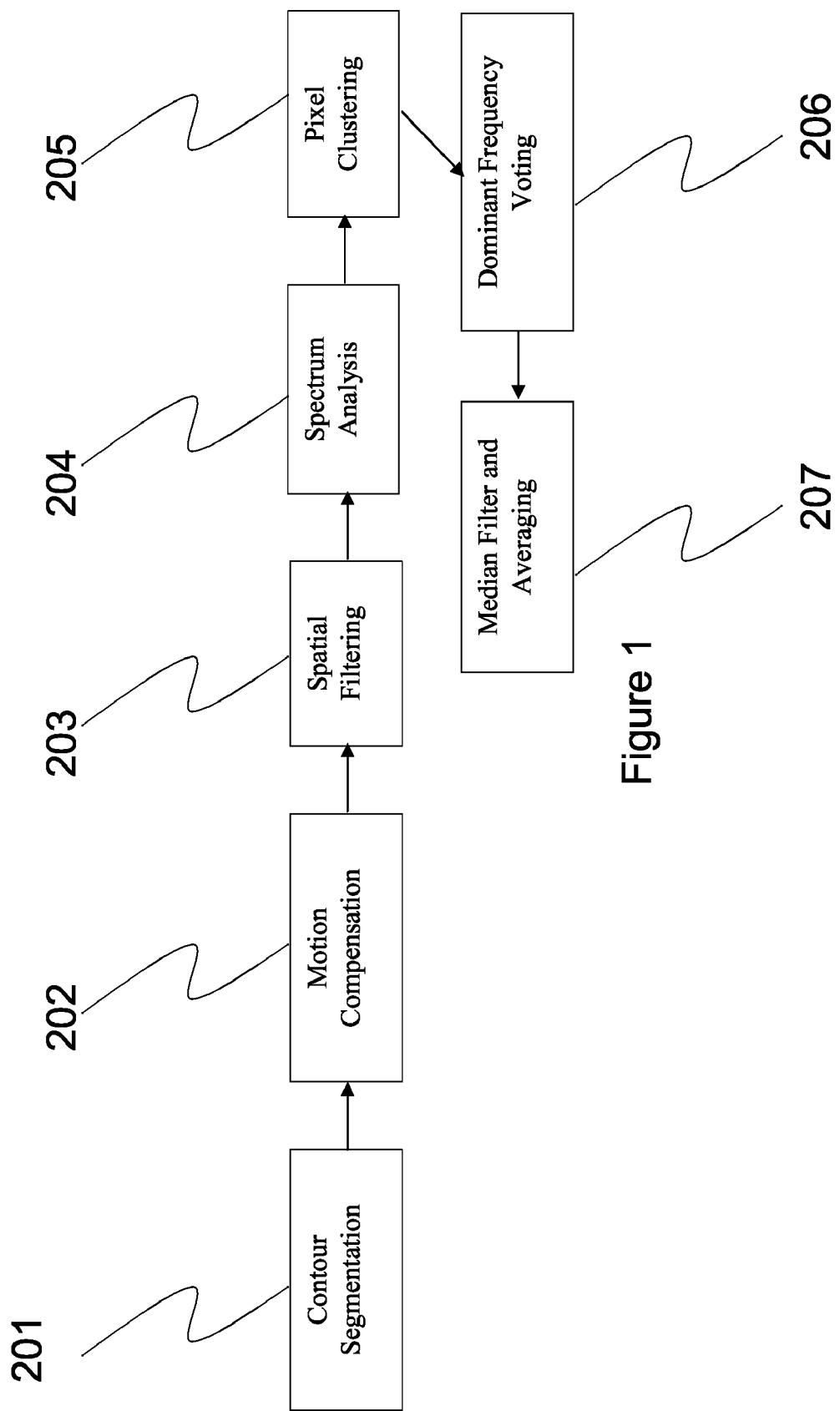
FIG. 1 depicts a block diagram of a method for vital sign measurement and estimation, according to one aspect of the present invention.

In the following detailed description, reference will be made to the accompanying drawing(s), in which identical functional elements are designated with like numerals. The aforementioned accompanying drawings show by way of illustration and not by way of limitation, specific embodiments and implementations consistent with principles of the present invention. These implementations are described in sufficient detail to enable those skilled in the art to practice the invention and it is to be understood that other implementations may be utilized and that structural changes and/or substitutions of various elements may be made without departing from the scope and spirit of present invention. The following detailed description is, therefore, not to be construed in a limited sense. Additionally, the various embodiments of the invention as described may be implemented in the form of software running on a general purpose computer, in the form of a specialized hardware, or combination of software and hardware.

The present invention relates to systems and methods for infrared video-based vital sign measurement using subject alignment, signal enhancement and harmonic analysis. More specifically, vital sign estimation is accomplished using contour segmentation and tracking, clustering of informative pixels of interests, and robust dominant frequency component estimation to improve performance over known systems for infrared video-based vital sign measurement.

To minimize the risk of harm caused by the measurement, contact-free vital sign detection through infrared light emitted by the human body itself is used. A passive infrared camera can detect the temperature modulation near superficial blood vessels due to pulsating blood flow or near the nasal area due to respiration. However, this detection is often complicated by subjects' movements, facial expressions, and occlusions of skin due to objects such as clothing, hair or jewelry. Therefore, robust subject alignment and motion compensation, signal enhancement and de-noising, and harmonic analysis in a low signal-to-noise ratio ("SNR") environment are critically needed to handle these challenges in practice. In one aspect, this system can measure the pulse and respiratory rate from passive thermal video by contour segmentation and tracking, clustering of informative pixels of interests, and robust dominant frequency component estimation, which relaxes the strong assumptions used in early research and improves the performance substantially. These assumptions-that a test subject does not move, and that the subject has artificial markers surrounding a rigid blood vessel, are not made here.

Since it is very hard for a human subject to remain completely still, every pixel needs to be aligned frame by frame in a video sequence in order to extract the temperature variation of a pixel over time. To achieve this, a robust auto segmentation and tracking algorithm—that is less affected by noise and subject movement—was designed for tracking a region near a superficial blood vessel. Compared with early approaches, this method does not need markers and can be computed at a very fast speed.

In addition, a signal detection model based on a thermal wave propagation hypothesis is used to reduce the signal cancellation caused by phase differences during regular averaging over a region. Since the low frequency thermal signal is several thousand times higher than temperature modulation caused by periodic blood flow, a non-linear filter is used to reduce the low-frequency signal leakage to the measurement range (in one embodiment, 40-100 beats per minute).

Finally, since not all pixels are informative for signal recovery, a clustering algorithm is used to efficiently concentrate informative pixels for the final measurement of beats per minute ("bpm").

1. Overview of Measurement System

FIG. 1 shows an overview of the vital sign measurement system and method according to one aspect of the invention. In this method, contour segmentation is first performed (step 201) to locate the blood vessel region to be measured. Then, the same set of segmentation parameters is used in all frames to segment the corresponding region. After that, motion compensation is preformed (step 202) by aligning all pixels in the selected region across frames based on the segmentation's position and scale in each frame.

After the contour segmentation and motion compensation, spatial filtering is performed (step 203) to remove noise not related to heart beat, and non-linear filtering is then performed (step 204) to process the temporal signal corresponding to each aligned pixel sequence. The signal spectrum of each pixel is then fed to a clustering algorithm for outlier removal (step 205). Pixels in the largest cluster are then used to select the dominant frequency (step 206), and the median of the dominant frequency is output as the pulse rate (step 207). This particular criterion, of selecting the largest cluster for outlier removal and using the median dominant frequency, can be improved with more information on the blood flow modulated pulse waveform.

2. Region of Interest Segmentation and Tracking

Figure 2:
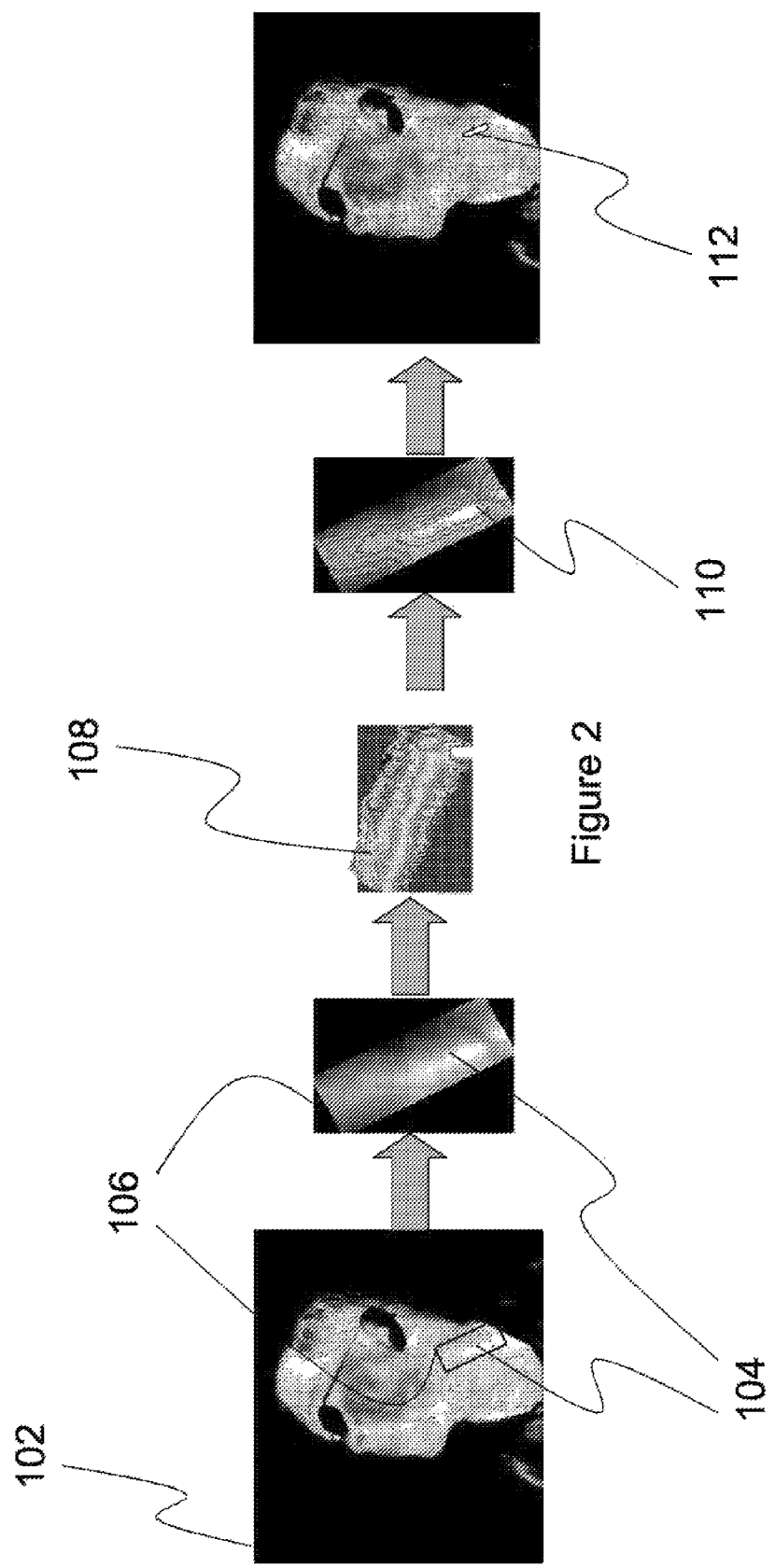
FIG. 2 depicts a photographic illustration of a Region of Interest ("ROI") segmentation procedure of a natural feature marker, according to one aspect of the present invention.

To improve upon existing motion tracking systems, natural features close to the blood vessel are used as a "marker" for the tracking and alignment task. In one embodiment, natural features refer to heat distribution in the diction region. FIG. 2 shows one embodiment of the segmentation procedure (step 201) of a natural feature marker. In one aspect, an frame 102 from a passive thermal video segment is selected, and an interest region 104 is roughly marked by hand with a large bounding box 106. The algorithm will then compute an isotherm 108 with a 0.1 Kelvin ("K") temperature step. This incremental temperature step is determined based on the temperature modulation level (0.08 K) and the sensitivity of the camera (0.025 K). More specifically, if the incremental temperature step is smaller than 0.08 K, the algorithm will not be able to get a stable estimate of the derivative of temperature variation. On the other hand, if the step is too large, the segmentation region may have large changes among various frames. After the isotherm 108 is constructed, the algorithm will determine the contour line 110 corresponding to the steepest temperature change. The contour found with this approach is least sensitive to small temperature variation. This contour property is used to mimic an artificial marker. Moreover, since the human body is not rigid, the contour inside the measurement region is affected less than artificial markers far away from the measurement region. This contour line 110 is then used to align pixels (not shown) inside the selected contour region 112. Since the selected region 112 inside the contour is very small, it is more reasonable to assume all pixels inside the selected contour region 112 belong to one rigid object. After contour tracking, pixels within the contour are aligned between frames based on the center and the size of the region. With aligned pixels, the algorithm can extract temperature variation over time.

3. Thermal Wave Propagation Hypothesis and Corresponding Measurement Model

Figure 3:
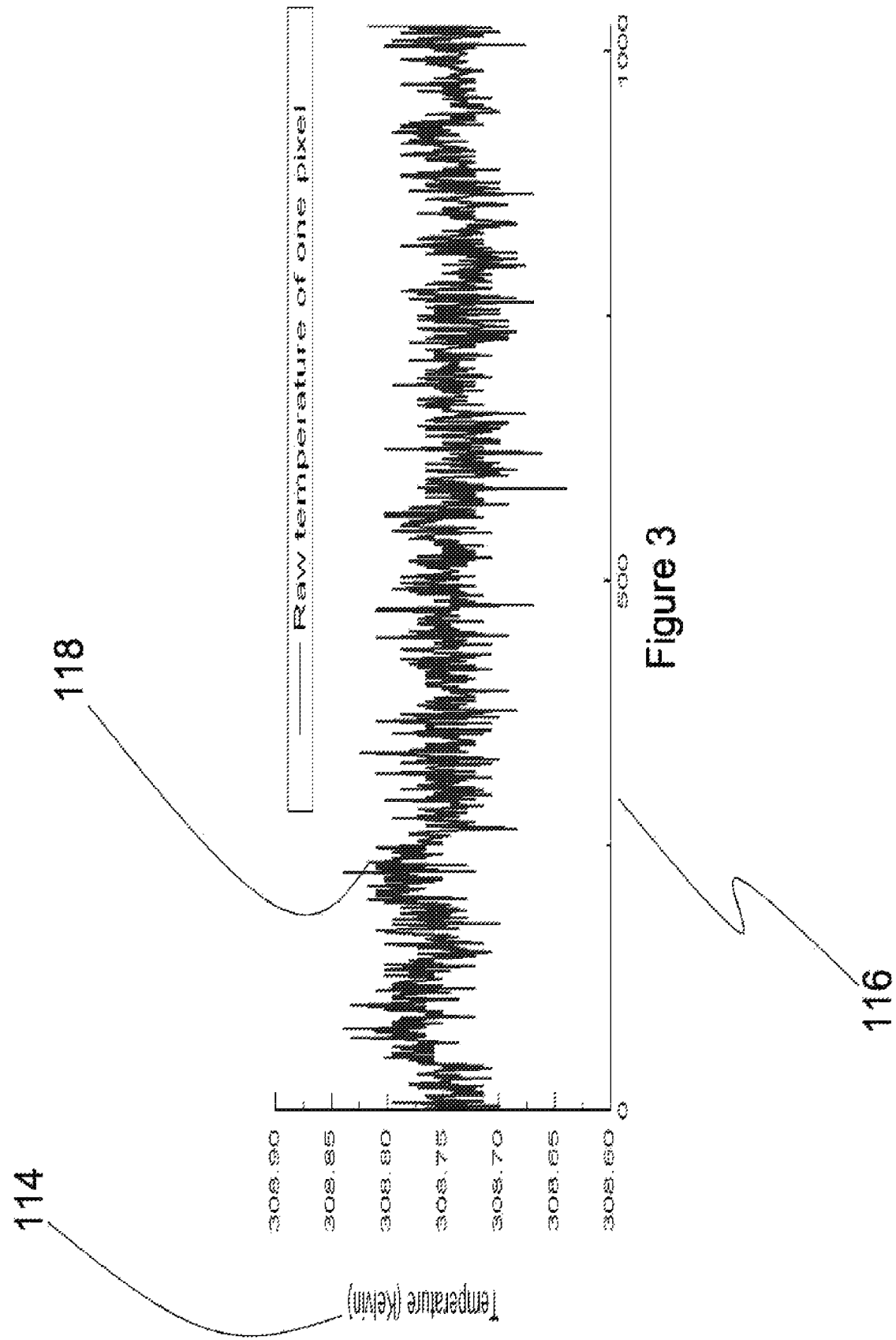
FIG. 3 depicts a chart of the temperature change over time of one pixel representing a superficial blood vessel in a thermal video, according to one aspect of the present invention.

FIG. 3 shows the temperature change 114 of one pixel (near a superficial blood vessel) over time 116. The raw temperature 118 of one pixel is represented over a period of frames per millisecond. In this particular illustration, the rate is approximately 115 frames per second (fps or f/s). This Figure reveals the difficulty of the estimation task. Since the temperature modulation caused by blood flow is too small compared with measurement noise, regular averaging over a region, a default approach for noise reduction in early approaches, is inadequate. This model can be improved for signal pickup by not using the peak value or simple average, but instead by weighting the signal based on the heat wave propagation assumption.

Because heat transfer needs time, a periodic heat change propagates in the form of a thermal wave in the human body. More specifically, the ideal temperature variation curves at two nearby locations close to a blood vessel are closely correlated and may have different phases. This is why the temperature change can be seen under the skin based on skin temperature change. With this in mind, the temperature variation on the skin surface near a superficial blood vessel has a location-dependent phase shift.

Temperature modulation signals with opposite phases may cancel each other if regular averaging is computed over a region and the region's dimension in the thermal wave propagation direction is larger than one wavelength. Since human blood flows at a fast speed along a major blood vessel (around 8.7 meters per second, according to S. Y. Chekmenev, A. A. Farag, E. A. Essock, Thermal Imaging of the Superficial Temporal Artery: An Arterial Pulse Recovery Model, *OTCBVS* 2007), and the blood vessel segment normally seen in the passive IR video is usually around 1 cm, the phase shift can be neglected along the blood vessel direction. On the other hand, the thermal wavelength λ can be computed with $$\lambda = 2\pi\sqrt{\frac{2K}{\omega}},$$

where K is the thermal diffusivity of the measured object and ω is signal frequency, as described in the Wübbenhorst reference cited above. In this particular aspect, the thermal diffusivity K for human skin was not used, but a similar substance, pork puree, has a thermal diffusivity of 0.1143-0.1180 centimeters squared per minute ($cm^2$/min). See Oregon State University; Thermal Properties; http://food.oregonstate.edu/energy/t11.html. In other references, the thermal diffusivity of water is listed at $(8.43-0.101 T) 10^{-3} cm^2$/sec, where T is temperature in the Celsius scale. D. W. James; The Thermal Diffusivity of Ice and Water between −40 and +60° C.; Journal of Materials Science; Springer Netherlands; Volume 3, Number 5; September, 1968; pp. 540-543. By using the thermal diffusivity of pork puree and an 80 bpm heart beat, a wavelength around 3.36 mm is obtained. This estimate is close to the wavelength on human skin surface.

Figure 4:
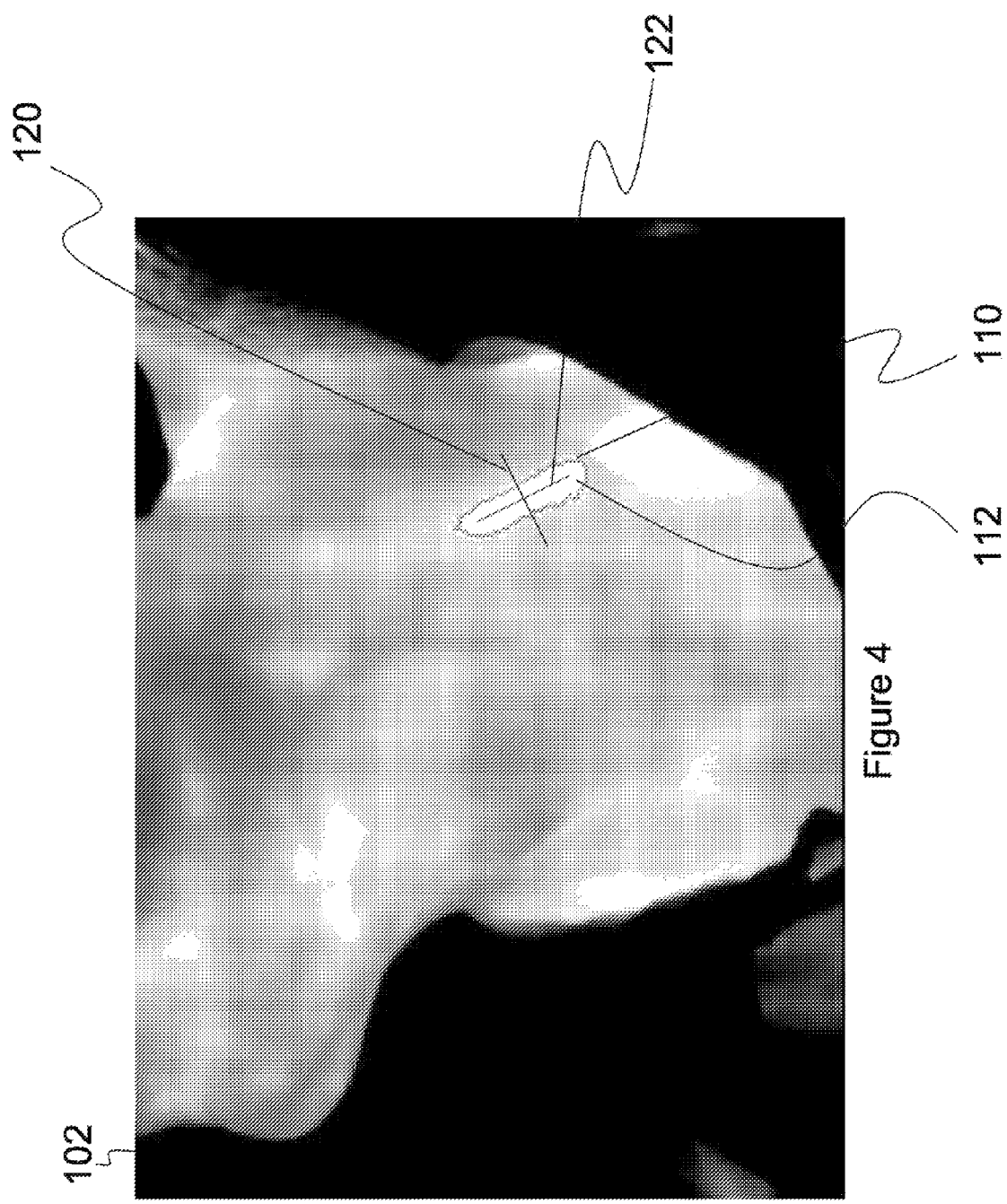
FIG. 4 depicts a close-up photographic illustration of a region near a blood vessel of a human, according to one aspect of the present invention.

If the thickness of the measured blood vessel is known, along with the distance of the blood vessel to skin surface and thermal diffusivity of various tissues, a more elaborate model can be built to pick up the modulation signal. Temporarily, in lieu of those parameters, a 1-D Gabor filter is used to average data on a jagged straight line 120 perpendicular to the blood vessel direction 122, as shown in FIG. 4. The Gabor filter is applied in the direction of the jagged straight line 120. Because the heat modulation around the blood vessel line 122 is close to even symmetry, only the real part of a complex Gabor filter is used. Since pixels have integer coordinates, it is hard to find pixels exactly on the jagged straight line 120. In this scenario, either a new pixel can be interpolated based on a small neighborhood or the 1-D Gabor filter can be changed a little to adapt to the pixels. Since it is preferable to not introduce additional noise to the original signal, the second approach is used in this particular aspect. More specifically, this algorithm finds pixels close to the jagged straight line 120 and computes the distance between the pixel and the blood vessel line 122. After the distance is computed, in one aspect, this distance is used to compute the Gabor filter coefficient, and this coefficient is then used to weigh the temperature value of a corresponding pixel. By using this Gabor filter, the low-frequency signals close to DC are significantly reduced. This will reduce the low-frequency signal (around 4000 times higher than the temperature modulation caused by blood flow) leakage to the measurement band (40-100 bpm) due to limited window size in the temporal frequency domain. This filter is compared with a regular averaging filter on close-up videos, and this filter does have an advantage over a regular averaging filter. For a video segment corresponding to the image frame 102 in FIG. 4, the heart beat tracking root mean square error ("RMSE") is reduced from 1.9 to 1.3 after using the Gabor filter, with all other parameters and algorithms set the same.

Because the thermal wavelength is very short, the model cannot work well when a measured blood vessel does not have enough pixels in each video frame. This model may also determine that if the pixel size is equivalent to the thermal wavelength, the temperature modulation detection will become very difficult because of the averaging filter zero point caused by the charge-coupled device ("CCD") pixel.

4. Signal Enhancement with Non-Linear Filtering of Temporal Signal

The window size used in the known systems is 512 points at a 30 Hz sampling rate. That window size limits the best frequency resolution to 0.059 Hz or 3.52 bpm. Since 3.52 bpm is much larger than the human heart beat variation in a short time, and a larger number compared to the lowest heart beat rate (e.g. 40 bpm), in one embodiment, a 2048-point window is used. In one aspect of the invention, to reduce possible aliasing, the sampling rate is increased to 60 Hz. The sample rate could also be set higher, at perhaps 115 Hz, although the result is similar to 60 Hz result. According to sampling theory, a 115 Hz sampling rate can sample signal frequency up to 57.5 Hz and a 60 Hz sampling rate can sample signal frequency up to 30 Hz. Since the human heart beat does not have much frequency component above 30 Hz, increasing sampling rate here will not help much.

Since the temperature modulation signal is 4000 or more times smaller than the low frequency temperature signal, and the lowest heart beat rate (around 40 bpm or 0.6 Hz) is a very low frequency signal compared with other signals, it is desired to find efficient ways to reduce signal leakage caused by limited window size (i.e., the heart beat spectral component can be hidden by the leakage from the larger component). Considering the magnitude of the DC value, blood-flow-caused temperature modulation and the frequency difference, a relatively simple approach to reduce disturbances from low frequency is a Hamming window. In another aspect, a Blackman-Harris window or Nuttall window can also be used. Disturbance signals were found close to the heart beat base frequency signal when the signal was processed; possibly caused by small movement of the blood vessel and nearby muscles. To reduce nearby nuisance disturbance and increase frequency estimation resolution, the frequency response main lobe should be narrower than the Hamming window. The length of sampling window can be increased to achieve that. However, that will increase the measurement time and decrease the response time of the system. Therefore, a 2048-point Fast Fourier Transform ("FFT") was first performed on the original signal. Then, a 2048-point FFT was preformed on a Hamming-windowed signal. After that, the point-by-point minimum of these two signals in the frequency domain is taken. The combined non-linear output has a narrow main lobe as a rectangular window.

Figure 5:
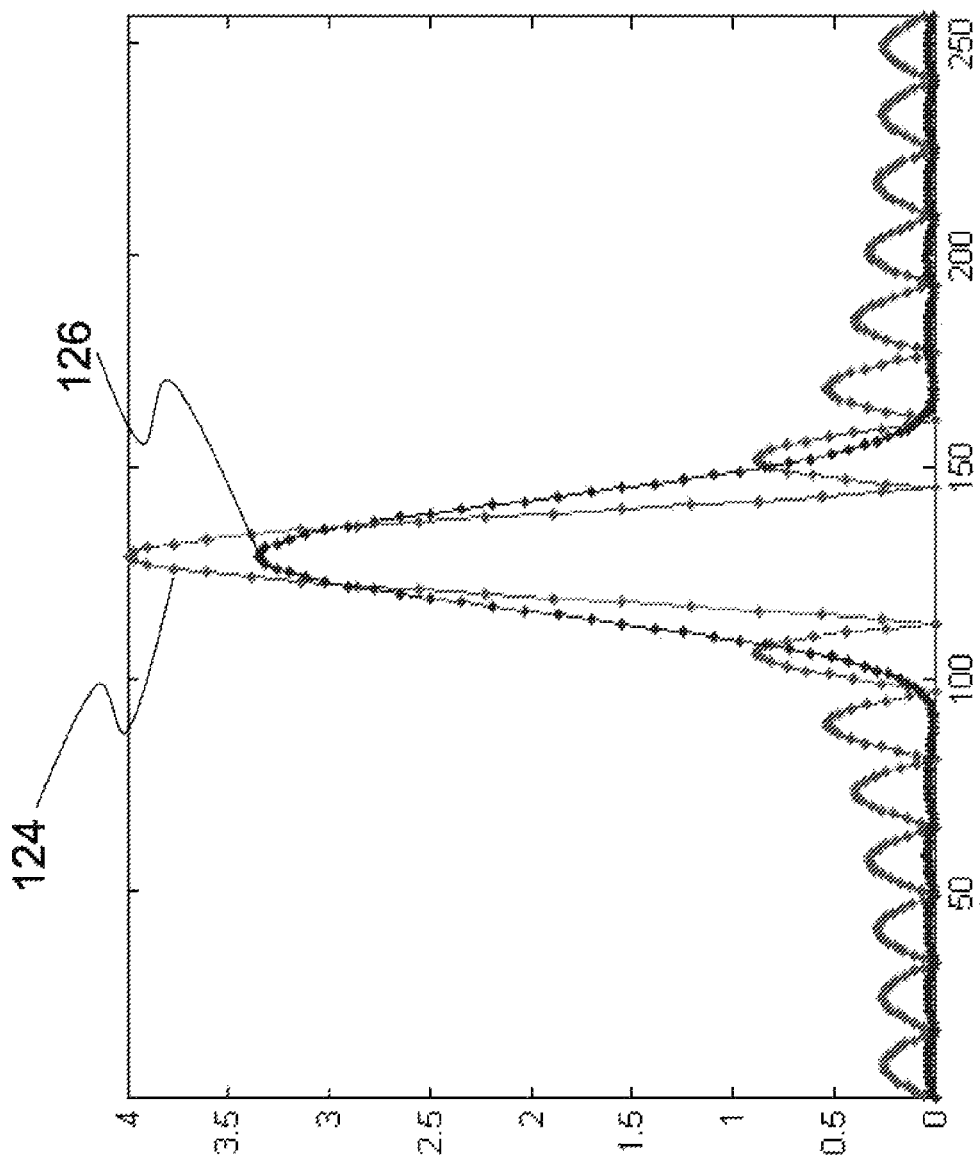
FIG. 5 depicts a chart of a frequency response of a normalized rectangular window and a Hamming window, according to one aspect of the present invention.

Moreover, it can even more efficiently reduce the signal leakage from a low frequency than a Hamming window. FIG. 5 shows frequency responses of a normalized rectangular window 124 and a Hamming window 126. As mentioned above, it is also possible to use the combination of a rectangular window with a Blackman-Harris window or a Nuttall window. Similar to the Hamming window, Blackman-Harris window and Nuttall windows also have low side lobes. Their side lobes are even lower than the Hamming window. Combining them with the rectangular window may lead to a better result than the combination of a Hamming window and a rectangular window.

5. Signal Clustering for Outlier Removal

In other methods, detection points are carefully marked for signal extraction. This is not a good automatic detection approach for several reasons. Since the operator cannot see the underlying temperature modulation signal, which is very small compared to the body temperature, it is hard to select points that have the most relevant information. Also, when there are waveforms for many pixels, it is very difficult to manually select good waveforms. To overcome this problem, in one aspect, a clustering algorithm was used in the signal extraction procedure to remove outliers.

By adjusting the 1-D Gabor filter location in the segmented region, tens or hundreds of waveforms can be obtained. A FFT is performed on these waveforms by using the approach described in section 4 above. Then, 18 dimension (for 115 Hz) or 34 dimension (for 60 Hz) data is picked, corresponding to the heart beat base rate (40-100 bpm) from each signal (2048 sampling points with 1024 dimension useful data), and the resulting data is fed into a simple K-means clustering program. In one embodiment, the number of clusters is heuristically set to 25. After the clustering, the algorithm selects the largest cluster as the cluster that has the heart beat signal, assuming outliers are sparsely distributed in the data space. If more prior knowledge of the waveform is available, a different criterion can be used to select clusters.

One known temporal signal extraction approach averages all pixels in the region of interest ("ROI") for each frame to get one temperature value for each frame. In contrast, the currently-described approach is more robust to short time disturbance in a small region. More specifically, if we use known methods, an impulse signal at one pixel in the ROI may set the final averaging value off. Frequent noise in the ROI region can make the final temporal signal very noisy. By extracting the temporal signal from each pixel and performing a cluster analysis, these disturbances are isolated and their impact on the final output efficiently reduced.

6. Computation of the Heart Beat Base Frequency

In one embodiment, the frequency peak of every point in the selected cluster is then used to vote in 18 bins (for 115 Hz frame rate) or 34 bins (for 60 Hz frame rate). The bin with highest vote is selected as the main peak and all bins in main peak ±2 range are used to compute an average estimation of the heartbeat. This voting/averaging approach has not been used in any previous algorithms.

7. Respiration Measurement

Figure 6:
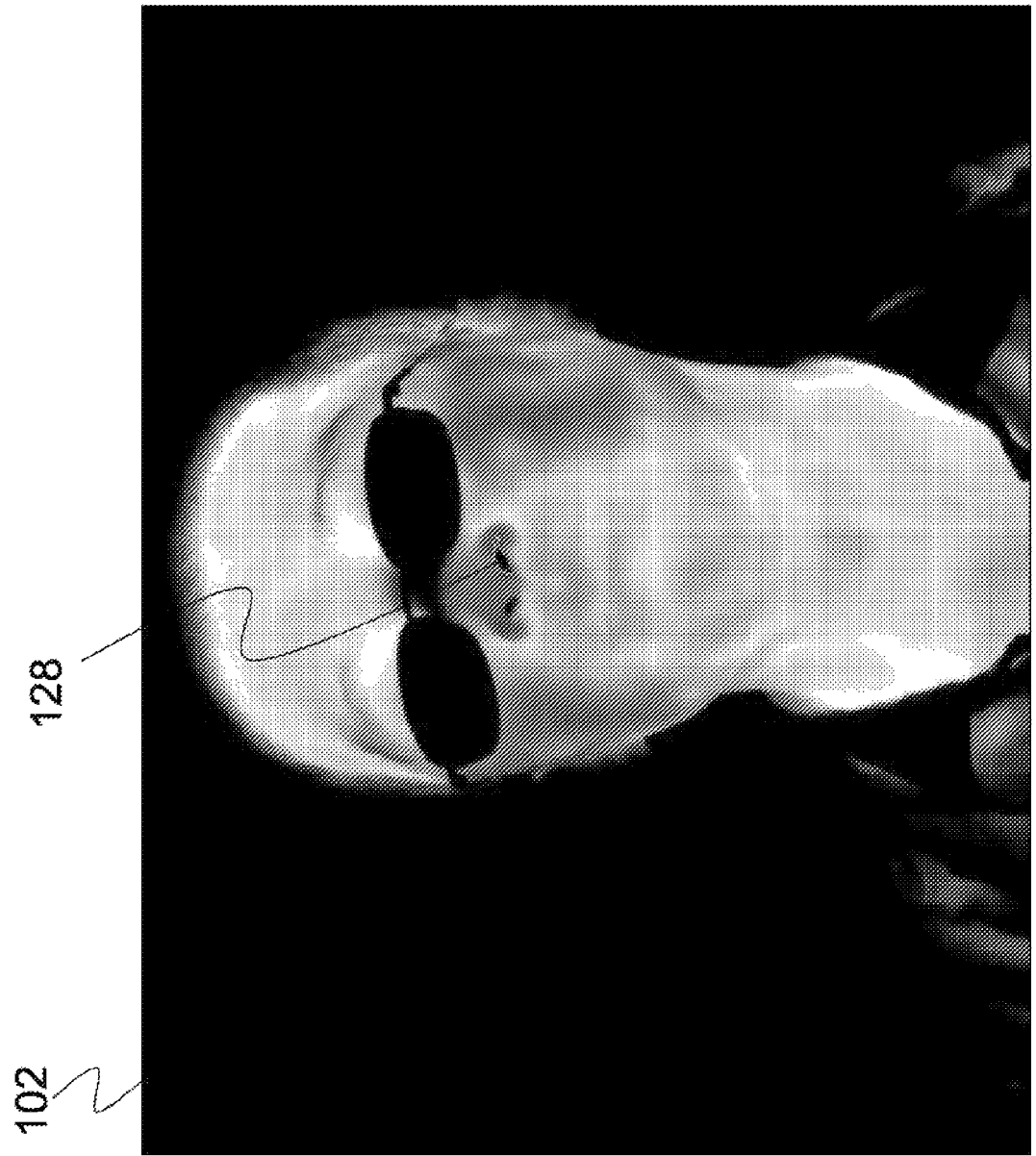
FIG. 6 depicts a photographic illustration of a passive thermal video of a human used for breath rate measurement, according to one aspect of the present invention.

In one embodiment, a similar ROI segmentation and tracking algorithm was used for breath rate measurement from nostril temperature variation. FIG. 6 shows a frame 102 and selected nostril region 128 used for this measurement. Since the signal from direct nostril temperature measurement is strong, peaks can be directly counted without complicated post-processing. A segmentation and tracking algorithm of this nature has not been previously used.

8. Experiments

During experimentation, a mid-wave infrared camera was used, which can capture infrared light in the range of 3.0~5.0 microns. The resolution of the camera is 640 by 512 lines by 14 bits. The temperature sensitivity of the camera was 0.025 K and the frame rates selected were 30, 60, and 115 frames per second ("fps").

To compare the IR video-based measurement with traditional sensor measurements, a piezolelectric pulse transducer, a piezolelectric respiration transducer and ECG electrodes were used, along with a PowerLab from ADInstruments to measure a subject's heart beat and respiration rate while IR video of the subject was captured (ADInstruments, Inc., Colorado Spring, Colo., 80906).

To verify the effectiveness of this approach, it was compared with the approach described in Sun et al. The comparison result is shown in Table 1. Because the algorithm described in Sun et al. required strictly still subjects, that algorithm cannot work on many of the sequences in the method described herein. On sequences where that algorithm can work, the inventive method and chosen algorithm consistently performed better than the known algorithm. This also aligns well with the most recent publication from that group, in Garbey et al.

TABLE 1

Pulse rate estimation results.

| Subject # | fps | # of frames | GT bpm | Est. bpm | Diff. bpm | RMSE | Est. bpm (S) | Diff. bpm (S) | RMSE (S) |
|---|---|---|---|---|---|---|---|---|---|
| 1 | 60.0 | 2500 | 66.3 | 63.0 | −3.3 | 3.9 | N/A | N/A | N/A |
| 2 | 60.0 | 3000 | 59.8 | 60.7 | +0.9 | 2.5 | 61.4 | +1.6 | 3.3 |
| 4 | 115.0 | 5000 | 64.0 | 65.0 | +1.0 | 3.8 | N/A | N/A | N/A |
| 5 | 60.0 | 3500 | 60.7 | 60.3 | −0.4 | 3.3 | 56.1 | −4.6 | 8.2 |
| 6 | 115.0 | 5000 | 78.9 | 80.1 | +1.2 | 1.9 | N/A | N/A | N/A |
| 7 | 115.0 | 5000 | 65.2 | 64.4 | −0.8 | 1.7 | N/A | N/A | N/A |
| 8 | 115.0 | 5000 | 62.8 | 66.2 | +3.4 | 4.2 | N/A | N/A | N/A |
| 9 | 115.0 | 5000 | 63.5 | 62.4 | −1.1 | 3.1 | N/A | N/A | N/A |
| 10 | 115.0 | 5000 | 73.3 | 72.6 | −0.7 | 1.8 | N/A | N/A | N/A |
| 11 | 30.0 | 2000 | 65.3 | 65.8 | +0.5 | 1.9 | N/A | N/A | N/A |
| 12 | 30.0 | 2000 | 66.6 | 63.9 | −2.7 | 3.9 | N/A | N/A | N/A |
| 14 | 30.0 | 1750 | 65.7 | 64.7 | −1.0 | 3.3 | N/A | N/A | N/A |
| 17 | 115.0 | 5000 | 86.6 | 87.9 | +1.3 | 4.9 | 88.9 | +2.3 | 5.8 |
| 18 | 115.0 | 5000 | 78.7 | 76.5 | −2.2 | 3.1 | N/A | N/A | N/A |
| 20 | 115.0 | 5000 | 75.3 | 74.7 | −0.7 | 1.9 | N/A | N/A | N/A |
| 22 | 115.0 | 5000 | 83.1 | 83.2 | +0.1 | 2.1 | N/A | N/A | N/A |
| 23 | 115.0 | 5000 | 67.2 | 68.2 | −1.0 | 1.3 | N/A | N/A | N/A |
| 28 | 115.0 | 5000 | 67.6 | 69.3 | +1.7 | 2.8 | 64.6 | −2.0 | 6.4 |

TABLE 1-continued

Pulse rate estimation results.

| Subject # | fps | # of frames | GT bpm | Est. bpm | Diff. bpm | RMSE | Est. bpm (S) | Diff. bpm (S) | RMSE (S) |
|---|---|---|---|---|---|---|---|---|---|
| 29 | 115.0 | 5000 | 68.7 | 70.1 | +1.4 | 2.9 | N/A | N/A | N/A |
| 30 | 60.0 | 3000 | 61.1 | 60.9 | −0.2 | 2.3 | N/A | N/A | N/A |

Figure 7:
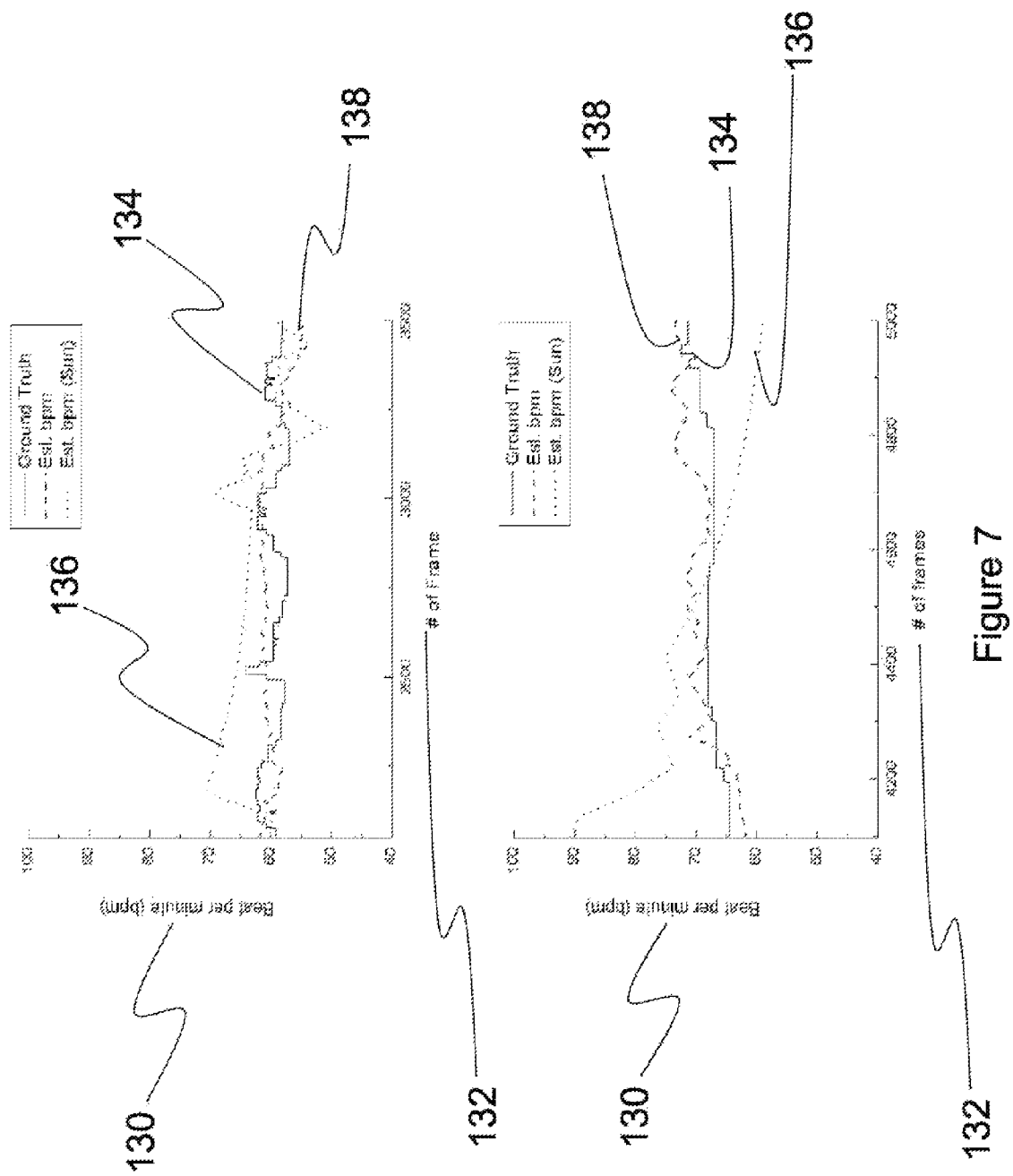
FIG. 7 depicts two charts of the pulse rate estimation results of one aspect of the invention and the results of known methods in the art.

Some literature only reported one average heart rate measured over several minutes. They did not report the stability of their algorithms for continuous measurement. In one aspect, an approach was designed to check the algorithm stability based on RMSE between two heart beat curves measured by ADInstrument devices and an IR camera, respectively. FIG. 7 shows the comparison results on two sequences that Sun et al.'s method can measure. The measurement of beats per minute 130 is taken over a period of several thousand frames of video 132. The ground truth measurement 134 is shown along with the pulse rate estimate using the Sun et. al. method 136 and the pulse rate estimate of the inventive method 138. In all these comparisons, the inventive method described herein constantly outperforms the known method. In an alternate embodiment, a speech pitch detection approach may be used on these sequences. One big difference between the heart beat detection and speech pitch detection is that the blood flow-caused temperature modulation is much noisier than a speech signal.

Various aspects of the present invention, whether alone or in combination with other aspects of the invention, may be implemented in C++ code running on a computing platform operating in a Windows XP environment. However, aspects of the invention provided herein may be implemented in other programming languages adapted to operate in other operating system environments. Further, methodologies may be implemented in any type of computing platform, including but not limited to, personal computers, mini-computers, mainframes, workstations, networked or distributed computing environments, computer platforms separate, integral to, or in communication with charged particle tools, and the like. Further, aspects of the present invention may be implemented in machine readable code provided in any memory medium, whether removable or integral to the computing platform, such as a hard disc, optical read and/or write storage mediums, RAM, ROM, and the like. Moreover, machine readable code, or portions thereof, may be transmitted over a wired or wireless network.

Figure 8:
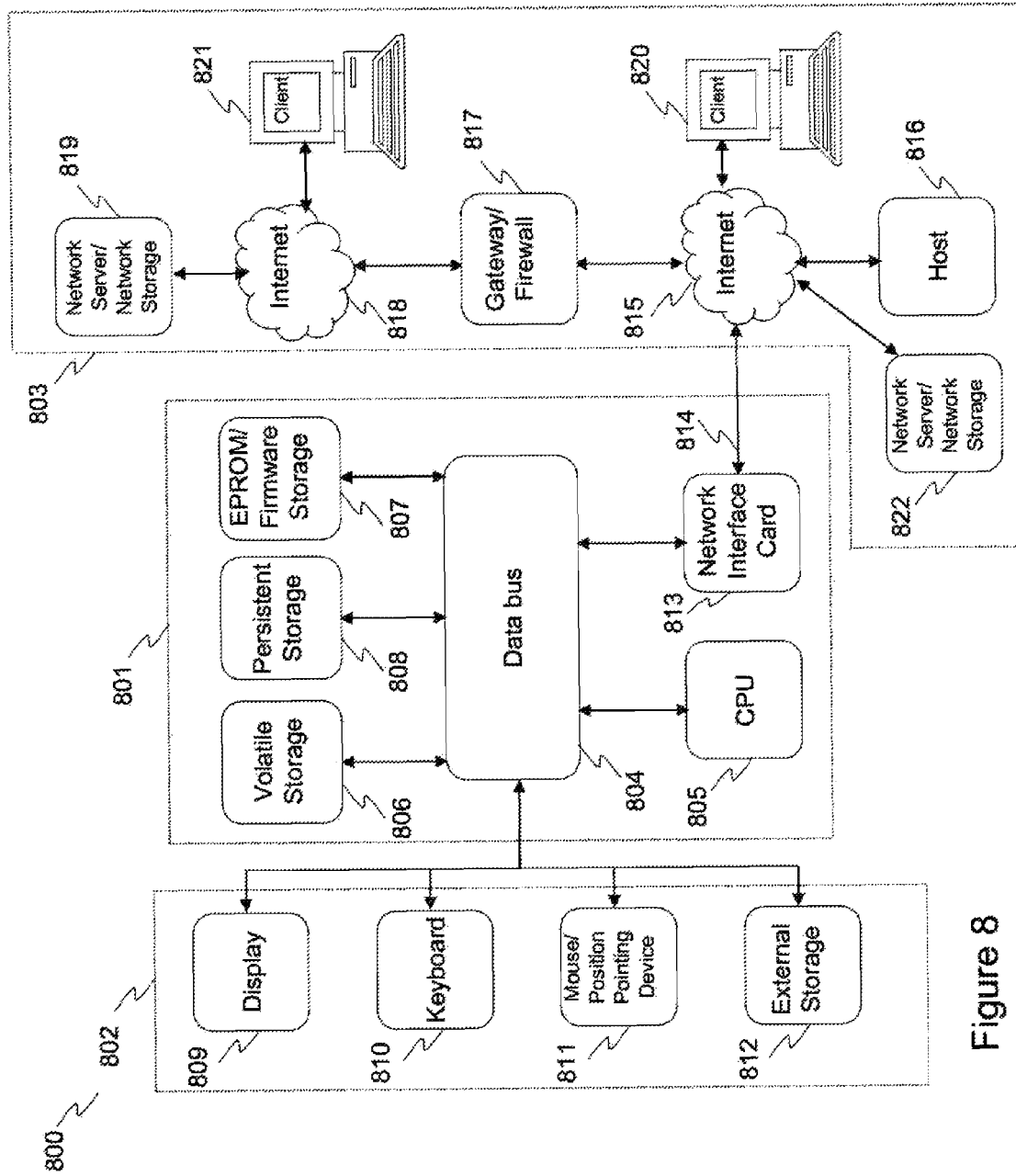
FIG. 8 illustrates an exemplary embodiment of a computer platform upon which the inventive system may be implemented.

FIG. 8 is a block diagram that illustrates an embodiment of a computer/server system 800 upon which an embodiment of the inventive methodology may be implemented. The system 800 includes a computer/server platform 801, peripheral devices 802 and network resources 803.

The computer platform 801 may include a data bus 804 or other communication mechanism for communicating information across and among various parts of the computer platform 801, and a processor 805 coupled with bus 801 for processing information and performing other computational and control tasks. Computer platform 801 also includes a volatile storage 806, such as a random access memory (RAM) or other dynamic storage device, coupled to bus 804 for storing various information as well as instructions to be executed by processor 805. The volatile storage 806 also may be used for storing temporary variables or other intermediate information during execution of instructions by processor 805. Computer platform 801 may further include a read only memory (ROM or EPROM) 807 or other static storage device coupled to bus 804 for storing static information and instructions for processor 805, such as basic input-output system (BIOS), as well as various system configuration parameters. A persistent storage device 808, such as a magnetic disk, optical disk, or solid-state flash memory device is provided and coupled to bus 801 for storing information and instructions.

Computer platform 801 may be coupled via bus 804 to a display 809, such as a cathode ray tube (CRT), plasma display, or a liquid crystal display (LCD), for displaying information to a system administrator or user of the computer platform 801. An input device 820, including alphanumeric and other keys, is coupled to bus 801 for communicating information and command selections to processor 805. Another type of user input device is cursor control device 811, such as a mouse, a trackball, or cursor direction keys for communicating direction information and command selections to processor 804 and for controlling cursor movement on display 809. This input device typically has two degrees of freedom in two axes, a first axis (e.g., x) and a second axis (e.g., y), that allows the device to specify positions in a plane.

An external storage device 812 may be connected to the computer platform 801 via bus 804 to provide an extra or removable storage capacity for the computer platform 801. In an embodiment of the computer system 800, the external removable storage device 812 may be used to facilitate exchange of data with other computer systems.

The invention is related to the use of computer system 800 for implementing the techniques described herein. In an embodiment, the inventive system may reside on a machine such as computer platform 801. According to one embodiment of the invention, the techniques described herein are performed by computer system 800 in response to processor 805 executing one or more sequences of one or more instructions contained in the volatile memory 806. Such instructions may be read into volatile memory 806 from another computer-readable medium, such as persistent storage device 808. Execution of the sequences of instructions contained in the volatile memory 806 causes processor 805 to perform the process steps described herein. In alternative embodiments, hard-wired circuitry may be used in place of or in combination with software instructions to implement the invention. Thus, embodiments of the invention are not limited to any specific combination of hardware circuitry and software.

The term "computer-readable medium" as used herein refers to any medium that participates in providing instructions to processor 805 for execution. The computer-readable medium is just one example of a machine-readable medium, which may carry instructions for implementing any of the methods and/or techniques described herein. Such a medium may take many forms, including but not limited to, non-volatile media, volatile media, and transmission media. Non-volatile media includes, for example, optical or magnetic disks, such as storage device 808. Volatile media includes dynamic memory, such as volatile storage 806. Transmission media includes coaxial cables, copper wire and fiber optics, including the wires that comprise data bus 804. Transmission media can also take the form of acoustic or light waves, such as those generated during radio-wave and infra-red data communications.

Common forms of computer-readable media include, for example, a floppy disk, a flexible disk, hard disk, magnetic tape, or any other magnetic medium, a CD-ROM, any other optical medium, punchcards, papertape, any other physical medium with patterns of holes, a RAM, a PROM, an EPROM, a FLASH-EPROM, a flash drive, a memory card, any other memory chip or cartridge, a carrier wave as described hereinafter, or any other medium from which a computer can read.

Various forms of computer readable media may be involved in carrying one or more sequences of one or more instructions to processor 805 for execution. For example, the instructions may initially be carried on a magnetic disk from a remote computer. Alternatively, a remote computer can load the instructions into its dynamic memory and send the instructions over a telephone line using a modem. A modem local to computer system 800 can receive the data on the telephone line and use an infra-red transmitter to convert the data to an infra-red signal. An infra-red detector can receive the data carried in the infra-red signal and appropriate circuitry can place the data on the data bus 804. The bus 804 carries the data to the volatile storage 806, from which processor 805 retrieves and executes the instructions. The instructions received by the volatile memory 806 may optionally be stored on persistent storage device 808 either before or after execution by processor 805. The instructions may also be downloaded into the computer platform 801 via Internet using a variety of network data communication protocols well known in the art.

The computer platform 801 also includes a communication interface, such as network interface card 813 coupled to the data bus 804. Communication interface 813 provides a two-way data communication coupling to a network link 814 that is connected to a local network 815. For example, communication interface 813 may be an integrated services digital network (ISDN) card or a modem to provide a data communication connection to a corresponding type of telephone line. As another example, communication interface 813 may be a local area network interface card (LAN NIC) to provide a data communication connection to a compatible LAN. Wireless links, such as well-known 802.11a, 802.11b, 802.11g and Bluetooth may also used for network implementation. In any such implementation, communication interface 813 sends and receives electrical, electromagnetic or optical signals that carry digital data streams representing various types of information.

Network link 813 typically provides data communication through one or more networks to other network resources. For example, network link 814 may provide a connection through local network 815 to a host computer 816, or a network storage/server 817. Additionally or alternatively, the network link 813 may connect through gateway/firewall 817 to the wide-area or global network 818, such as an Internet. Thus, the computer platform 801 can access network resources located anywhere on the Internet 818, such as a remote network storage/server 819. On the other hand, the computer platform 801 may also be accessed by clients located anywhere on the local area network 815 and/or the Internet 818. The network clients 820 and 821 may themselves be implemented based on the computer platform similar to the platform 801.

Local network 815 and the Internet 818 both use electrical, electromagnetic or optical signals that carry digital data streams. The signals through the various networks and the signals on network link 814 and through communication interface 813, which carry the digital data to and from computer platform 801, are exemplary forms of carrier waves transporting the information.

Computer platform 801 can send messages and receive data, including program code, through the variety of network(s) including Internet 818 and LAN 815, network link 814 and communication interface 813. In the Internet example, when the system 801 acts as a network server, it might transmit a requested code or data for an application program running on client(s) 820 and/or 821 through Internet 818, gateway/firewall 817, local area network 815 and communication interface 813. Similarly, it may receive code from other network resources.

The received code may be executed by processor 805 as it is received, and/or stored in persistent or volatile storage devices 808 and 806, respectively, or other non-volatile storage for later execution. In this manner, computer system 801 may obtain application code in the form of a carrier wave.

Finally, it should be understood that processes and techniques described herein are not inherently related to any particular apparatus and may be implemented by any suitable combination of components. Further, various types of general purpose devices may be used in-accordance with the teachings described herein. It may also prove advantageous to construct specialized apparatus to perform the method steps described herein. The present invention has been described in relation to particular examples, which are intended in all respects to be illustrative rather than restrictive. Those skilled in the art will appreciate that many different combinations of hardware, software, and firmware will be suitable for practicing the method for vital sign estimation. For example, the described software may be implemented in a wide variety of programming or scripting languages, such as Assembler, C/C++, perl, shell, PHP, Java, etc.

Although various representative embodiments of this invention have been described above with a certain degree of particularity, those skilled in the art could make numerous alterations to the disclosed embodiments without departing from the spirit or scope of the inventive subject matter set forth in the specification and claims. In methodologies directly or indirectly set forth herein, various steps and operations are described in one possible order of operation, but those skilled in the art will recognize that steps and operations may be rearranged, replaced, or eliminated without necessarily departing from the spirit and scope of the present invention. Also, various aspects and/or components of the described embodiments may be used singly or in any combination in the computerized storage system for capturing, classifying and linking collaboratively-captured media. It is intended that all matter contained in the above description or shown in the accompanying drawings shall be interpreted as illustrative only and not limiting.

What is claimed is:

1. A system for estimating vital signs from passive thermal video comprising:
   an infrared video receiving module for receiving an infrared video segment of a subject;
   a contour segmentation module for contour segmenting the video segment to select a region of pixels representing a portion of the subject;
   an alignment module for aligning the selected region of pixels across a plurality of frames of the video segment;
   a signal detection module for detecting a signal from the selected region using a thermal wave propagation-based signal detection method;

a spatial filtering module for spatial filtering the signal to remove noise not related to the vital signs to be estimated;
a non-linear temporal filtering module to process a temporal signal corresponding to each aligned pixel sequence;
an clustering module for removing outliers of the signal using a pixel clustering algorithm;
a frequency selection module for selecting a frequency peak of the signal using a dominant frequency voting technique that generates a plurality of bins based on a sampling rate, each of the plurality of bins representing a possible frequency peak of the signal, votes on each of the plurality of bins and selects the frequency peak having a highest number of votes; and
an averaging module for averaging the selected frequency peak to compute an average estimation of at least one vital sign.

2. The system of claim 1, wherein the contour segmentation module further includes a natural feature module for selecting natural features close to the selected region.

3. The system of claim 2, wherein the contour segmentation module further includes a temperature selection module for selecting an isotherm temperature based on temperature modulation dynamic range and camera sensitivity.

4. The system of claim 3, wherein the contour segmentation module further includes a contour selection module for selecting a contour line corresponding to the steepest temperature change in the selected region.

5. The system of claim 4, wherein the selected region of pixels corresponds to a blood vessel.

6. The system of claim 1, wherein the spatial filtering module further includes a frequency response computation module for computing the frequency responses of the signal using a normalized rectangular window and a Hamming window.

7. A method for estimating vital signs from a passive thermal video comprising the steps of
receiving an infrared video segment of a subject;
contour segmenting the video segment to select a region of pixels representing a portion of the subject;
aligning the selected region of pixels across a plurality of frames of the video segment;
detecting a signal from the selected region using a thermal wave propagation-based signal detection method;
spatial filtering the signal to remove noise not related to the vital signs to be estimated;
performing non-linear filtering on the signal corresponding to each aligned pixel of the selected region;
removing outliers of the signal using a pixel clustering algorithm;
selecting a frequency peak of the signal using a dominant frequency voting technique that generates a plurality of bins based on a sampling rate, each of the plurality of bins representing a possible frequency peak of the signal, votes on each of the plurality of bins and selects the frequency peak having a highest number of votes; and
averaging the selected frequency peak to compute an average estimation of at least one vital sign.

8. The method of claim 7, wherein the step of contour segmenting the video segment further includes selecting natural features close to the selected region.

9. The method of claim 8, wherein the step of contour segmenting the video segment further includes selecting an isotherm temperature based on temperature modulation dynamic range and camera sensitivity.

10. The method of claim 9, wherein the step of contour segmenting the video segment further includes selecting a contour line corresponding to the steepest temperature change in the selected region.

11. The method of claim 10, wherein the step of contour segmenting the video segment further includes selecting a region of pixels corresponding to a blood vessel.

12. The method of claim 7, wherein the step of spatial filtering the signal to remove noise further includes computing the frequency responses of the signal using a normalized rectangular window and a Hamming window.

13. A computer program product embodied on a non-transitory computer readable medium for estimating vital signs from passive thermal video comprising computer program code for:
receiving an infrared video segment of a subject;
contour segmenting the video segment to select a region of pixels representing a portion of the subject;
aligning the selected region of pixels across a plurality of frames of the video segment;
detecting a signal from the selected region using a thermal wave propagation-based signal detection method;
spatial filtering the signal to remove noise not related to the vital signs to be estimated;
performing non-linear filtering on the signal corresponding to each aligned pixel of the selected region;
removing outliers of the signal using a pixel clustering algorithm;
selecting a frequency peak of the signal using a dominant frequency voting technique that generates a plurality of bins based on a sampling rate, each of the plurality of bins representing a possible frequency peak of the signal, votes on each of the plurality of bins and selects the frequency peak having a highest number of votes; and
averaging the selected frequency peak to compute an average estimation of at least one vital sign.

14. The computer program product of claim 13, further comprising computer program code for contour segmenting the video segment by selecting natural features close to the selected region.

15. The computer program product of claim 14, further comprising computer program code for contour segmenting the video segment by selecting an isotherm temperature based on temperature modulation dynamic range and camera sensitivity.

16. The computer program product of claim 15, further comprising computer program code for contour segmenting the video segment by selecting a contour line corresponding to the steepest temperature change in the selected region.

17. The computer program product of claim 16, further comprising computer program code for selecting a region of pixels that corresponds to a blood vessel.

18. The computer program product of claim 13, further comprising computer program code for spatial filtering the signal to remove noise by computing the frequency responses of the signal using a normalized rectangular window and a Hamming window.

19. The system of claim 4, wherein the selected region of pixels corresponds to a nostril.

20. The system of claim 1, wherein averaging the selected frequency peak comprises averaging the selected frequency peak with adjacent ones of the possible frequency peaks in numerical value.

* * * * *